(12) United States Patent
Cerundolo

(10) Patent No.: US 6,488,033 B1
(45) Date of Patent: Dec. 3, 2002

(54) OSTEOCHONDRAL TRANSPLANT TECHNIQUES

(75) Inventor: Daniel G. Cerundolo, Hingham, MA (US)

(73) Assignee: Cryolife, Inc., Kennesaw, GA (US)

(*) Notice: Subject to any disclaimer, the term of this patent is extended or adjusted under 35 U.S.C. 154(b) by 0 days.

(21) Appl. No.: 09/571,363

(22) Filed: May 15, 2000

(51) Int. Cl.⁷ .............................................. A61B 19/00
(52) U.S. Cl. ...................................................... 128/898
(58) Field of Search ...................... 128/898; 623/18.11, 623/18.12, 19.11–19.14, 20.14, 20.16, 20.22

(56) References Cited

U.S. PATENT DOCUMENTS

| | | |
|---|---|---|
| 4,461,281 A * 7/1984 | Carson ........................ 128/898 |
| 5,211,647 A 5/1993 | Schmieding |
| 5,320,626 A 6/1994 | Schmieding |
| 5,336,240 A 8/1994 | Metzler et al. |
| 5,391,171 A 2/1995 | Schmieding |
| 5,397,357 A 3/1995 | Schmieding et al. |
| 5,415,651 A 5/1995 | Schmieding |
| 5,423,823 A 6/1995 | Schmieding |
| 5,425,733 A 6/1995 | Schmieding |
| 5,458,604 A 10/1995 | Schmieding |
| 5,466,243 A 11/1995 | Schmieding et al. |
| 5,513,662 A * 5/1996 | Morse et al. ................ 128/898 |
| 5,575,801 A 11/1996 | Habermeyer et al. |
| 5,601,562 A 2/1997 | Wolf et al. |
| 5,620,448 A 4/1997 | Puddu |
| 5,626,613 A 5/1997 | Schmieding |
| 5,681,333 A 10/1997 | Burkhart et al. |
| 5,690,677 A 11/1997 | Schmieding et al. |
| 5,693,401 A 12/1997 | Sommers et al. |
| 5,713,374 A * 2/1998 | Pachence et al. ........... 128/898 |
| 5,749,875 A 5/1998 | Puddu |
| 5,782,835 A * 7/1998 | Hart et al. ................... 606/172 |
| 5,785,714 A 7/1998 | Morgan et al. |
| 5,895,425 A 4/1999 | Grafton et al. |
| 5,918,604 A 7/1999 | Whelan |
| 5,919,196 A 7/1999 | Bobic et al. |
| 6,179,871 B1 * 1/2001 | Halpern ....................... 128/898 |

OTHER PUBLICATIONS

Fresh Osteochondral Allografts for Treatment of Articular Defects in Osteochondritis Dissecans of the Lateral Femoral Condyle in Adults, Clinical Orthopaedics, Jun., 1994, vol. 303.

Osteochondral Allografts for Reconstruction of Articular Defects, Chapter 25, Operative Arthoscopy, Second Edition, edited by J.B. McGinty, R.R. Caspan, 1996.

Osteochondritis Dissecans, John C. Garrett, MD, Clinics in Sports Medicine, vol. 10, No. 3, Jul. 1991.

The Operative Technique of Fresh Osteochondral Allografting of the Knee; Operative Techniques in Orthopaedics, vol. 7, No. 4 ()Oct.), 1997, pp. 340–344.

Fresh Osteochondral Allografts for Post–Traumatic Knee Defects: Surgical Technique, Operative Techniques in Orthopaedics, vol. 7, No. 4 (Oct.), 1997, pp. 334–3339.

Fresh Osteochondral Allografts For Post–Traumatic Knee Defects: Surgical Technique, Operative Techniques in Orthopaedics, vol. 7, No. 4 (Oct.), 1997, pp. 334–339.

Osteochondral Allografts For Reconstruction of Articular Defects of The Knee, John C. Garrett, M.D., Osteochondral Allografts for Reconstruction of Articular Defects, Mar. 1997.

* cited by examiner

Primary Examiner—Corrine McDermott
Assistant Examiner—Hieu Phan
(74) Attorney, Agent, or Firm—Nixon & Vanderhye P.C.

(57) ABSTRACT

Osteoarticular allografts are transplanted by techniques which ensure substantial surface contour matching. Specifically, surgical techniques are provided whereby a plug from an osteochondral allograft may be transplanted to a cavity site which remains after a condylar defect is removed from a patient's condyle. In this regard, the present invention essentially includes placing an osteochondral allograft in substantially the same orientation as the patient condyle, and then removing the transplantable plug therefrom and forming the cavity site in the patient condyle while maintaining their relative same orientation. In this manner, the surface of the transplanted plug is matched to the contour of the excised osteochondral tissue.

12 Claims, 11 Drawing Sheets

Figure 3:
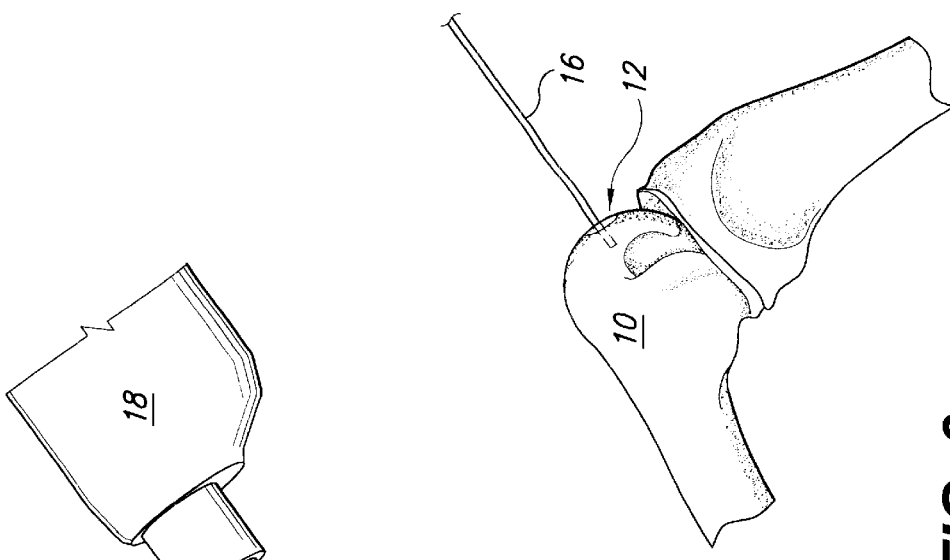

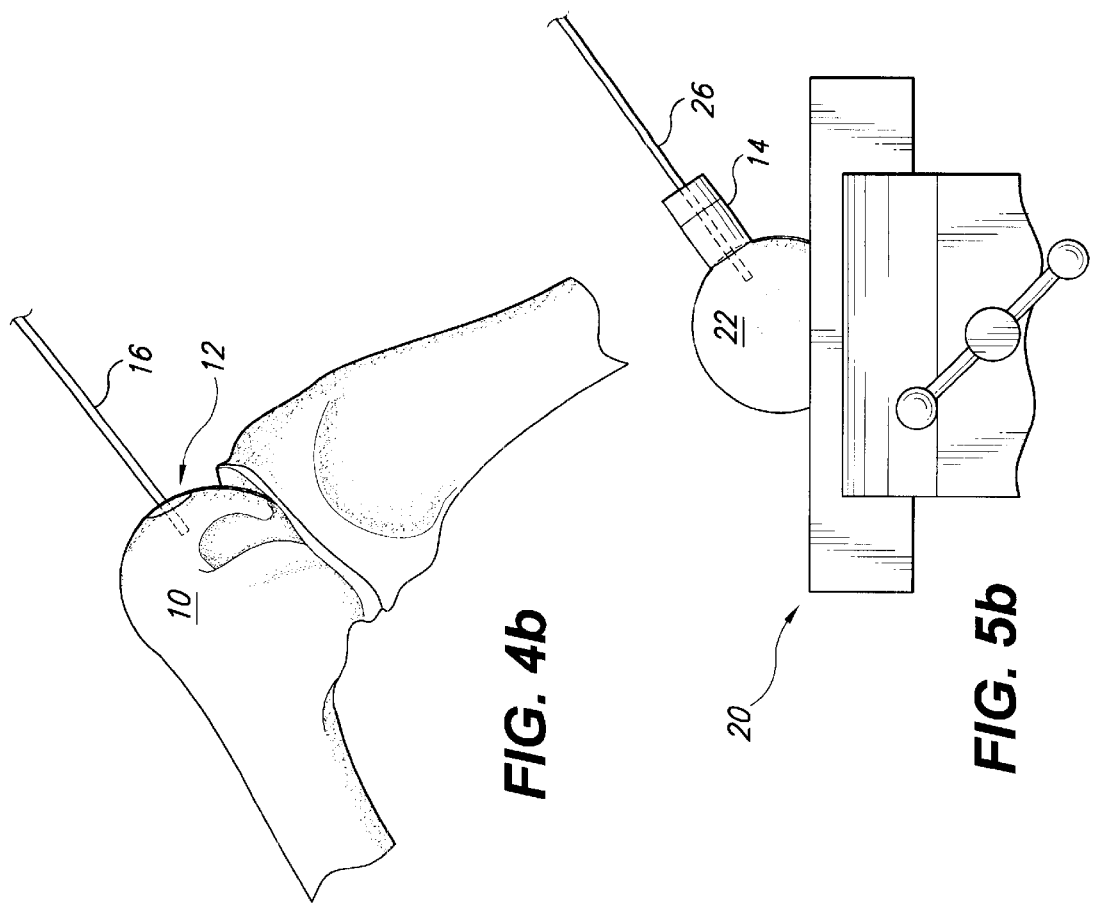
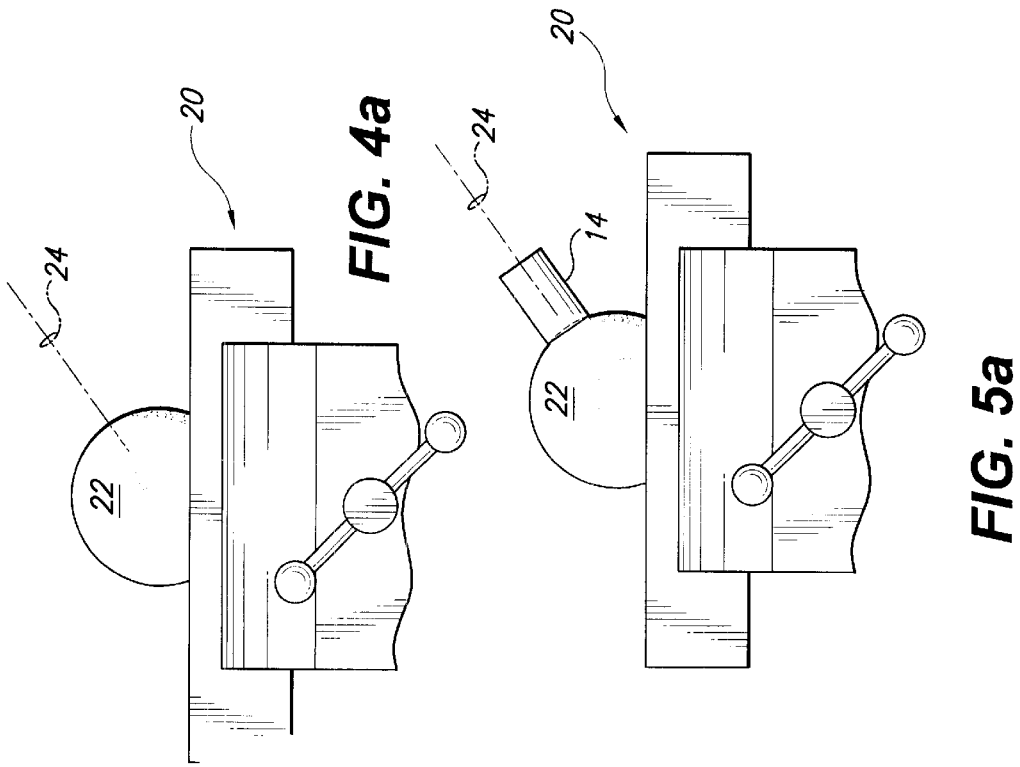

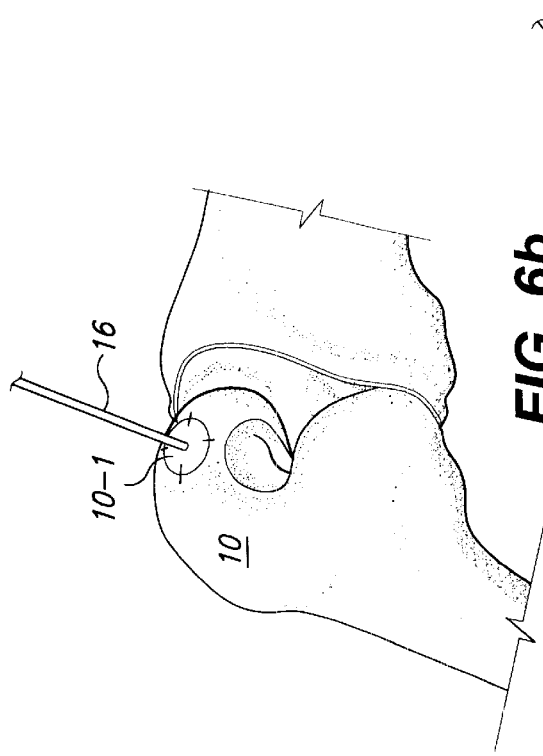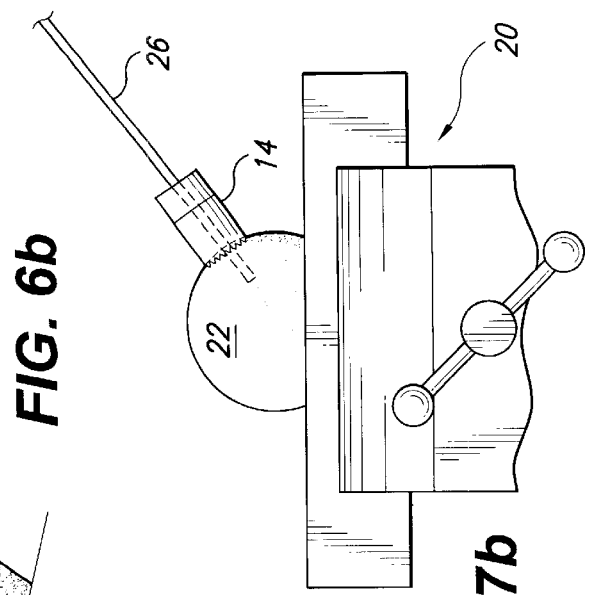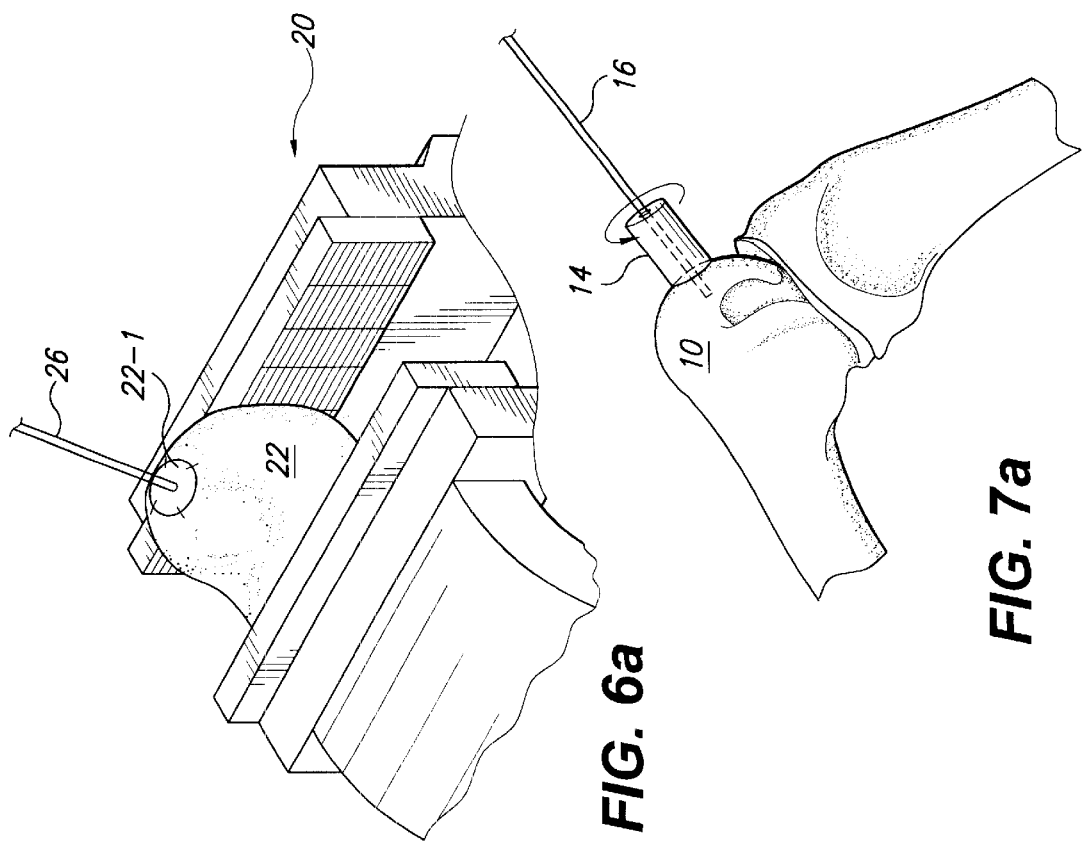

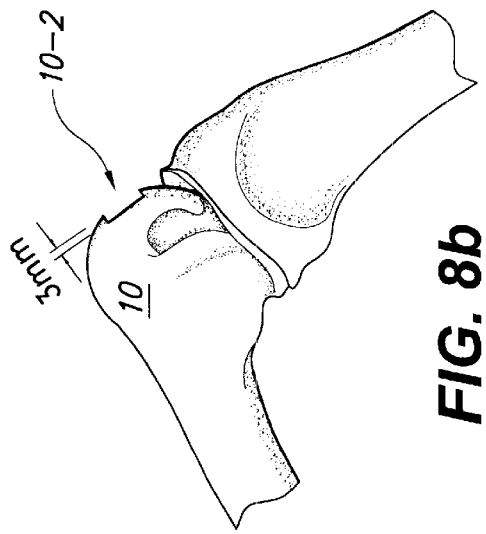
FIG. 8b
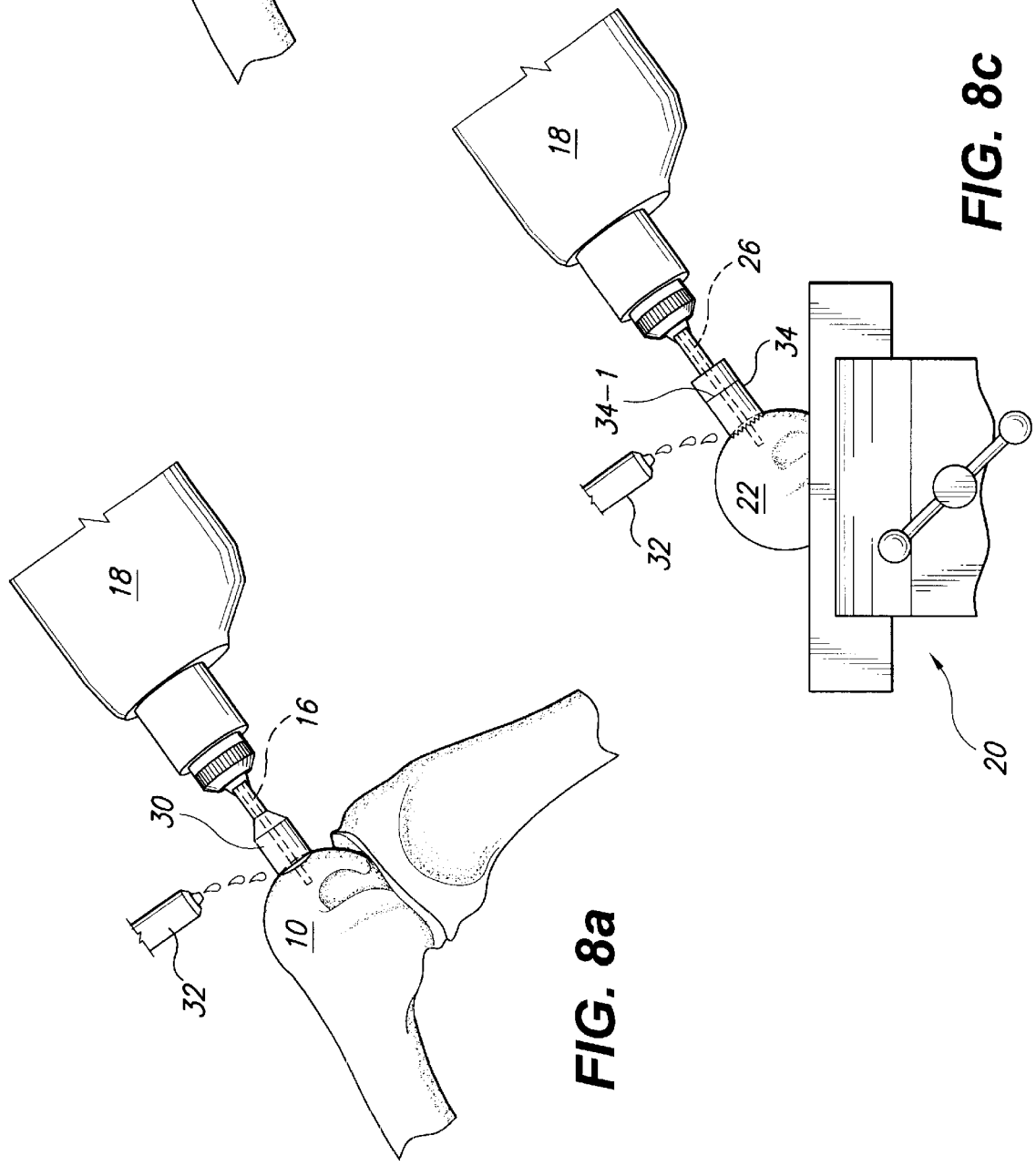
FIG. 8c
FIG. 8a

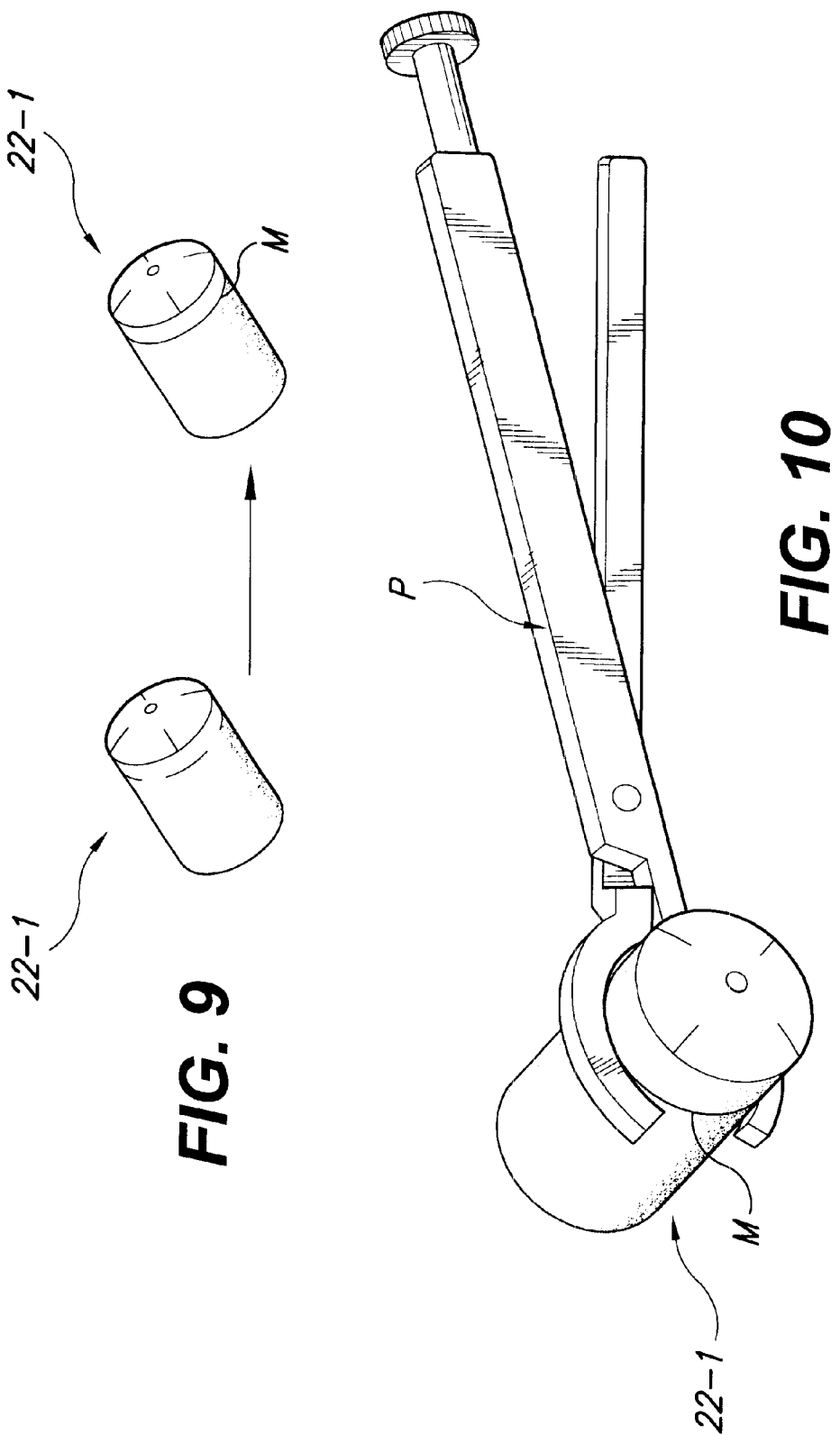

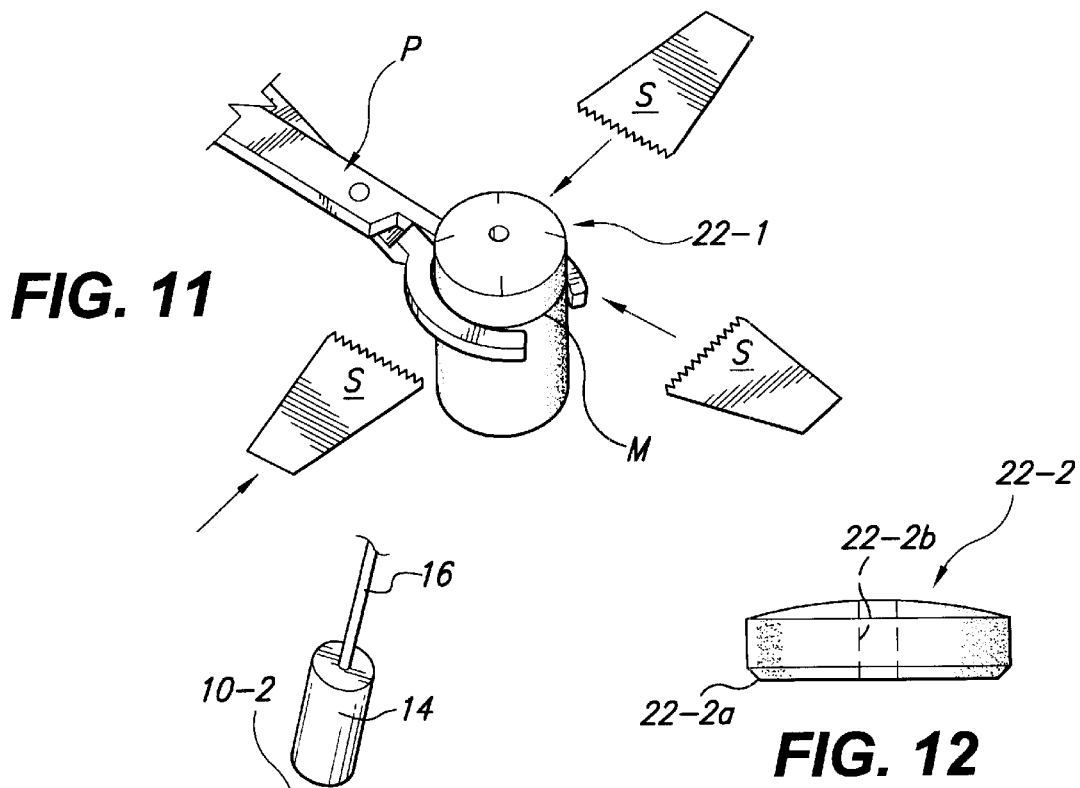
FIG. 11
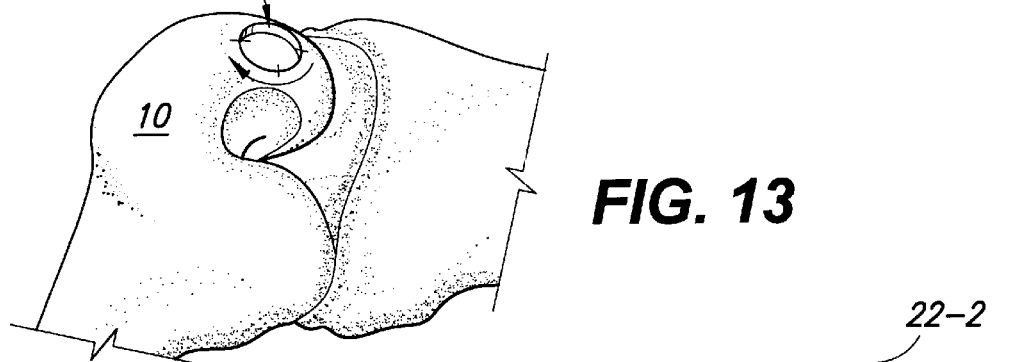
FIG. 12
FIG. 13
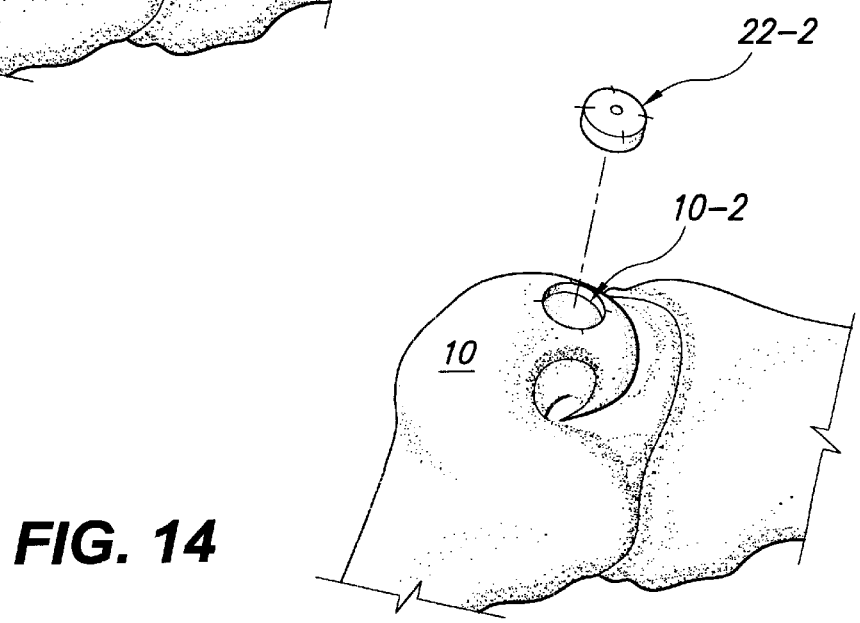
FIG. 14

OSTEOCHONDRAL TRANSPLANT TECHNIQUES

FIELD OF THE INVENTION

The present invention relates generally to surgical transplant techniques. More specifically, the present invention relates to techniques by which donor osteochondral allografts may be transplanted to a patient recipient.

BACKGROUND AND SUMMARY OF THE INVENTION

Bone transplantation has been a common surgical procedure for a number of years. In this regard, conventional bone transplantation typically involves removing a bone plug from another site from the same patient (i.e., an autograft) and then inserting the plug at a different site in need of the same. Transplantation of bone from another donor (i.e., an allograft) has also been used where autograft bone is not available. Allograft bone is processed in several ways and is available in solid, paste, or particulate matter.

In recent years, surgeons have been using osteoarticular autografts to repair small defects in the femoral condyle. Small plugs are taken from remote areas of the condyle and transplanted to areas which have defects and are more critical. Osteoarticular allografts, however, have not typically been used because osteoarticular cartilage cells do not survive the freezing or cryopreservation process. Recent advances in preservation of fresh articular cartilage have, however, made the use of osteoarticular cartilage allografts more common.

Instrumentation for bone plug transplantation has yielded plugs of a specified diameter. See in this regard, U.S. Pat. Nos. 5,782,835 and 5,919,196, the entire content of each being incorporated expressly hereinto by reference. The surface characteristics of autograft plugs have not been a consideration in selection or harvesting. In transplanting articular allografts, however, these surface characteristics are critical. In order for the allograft to be successful, the surface of the transplanted plug must have the same contour as the excised osteochondral tissue. If this contour is not correct, the articular surfaces of both the femur and tibia are at risk for damage.

According to the present invention, osteoarticular allografts are transplanted by techniques which ensure substantial surface contour matching. Broadly, the present invention is embodied in surgical techniques whereby a plug from an osteochondral allograft may be transplanted to a cavity site which remains after a condylar defect is removed from a patient's condyle. In this regard, the present invention essentially includes placing an osteochondral allograft in substantially the same orientation as the patient condyle, and then removing the transplantable plug therefrom and forming the cavity site in the patient condyle while maintaining their relative same orientation. In this manner, the surface of the transplanted plug is matched to the contour of the excised osteochondral tissue.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals denote like structural elements, and wherein FIGS. 1–15 collectively depict in a schematic fashion a particularly preferred transplantation technique according to one embodiment of the present invention; and FIGS. 16–19 collectively depict in a schematic fashion a transplantation technique according to another embodiment of the present invention.

DETAILED DESCRIPTION OF THE INVENTION

One particularly preferred technique for transplanting osteoarticular allografts according to the present invention is depicted schematically in accompanying FIGS. 1–15. In this regard, the patient is prepared initially by the surgeon making an incision along the lateral border of the patella. The patella is drawn back medially in order to expose the patient's condyle 10. The condylar defect 12 is visually identified by the attending surgeon and a bone cutter/guide 14 selected which is of sufficient size so as to bound entirely the identified defect 12. Conventional sizes of the bone cutter/guide 14 that may be selected include, for example, 20, 25, 30 or 35 mm diameter cutters.

Figure 2:
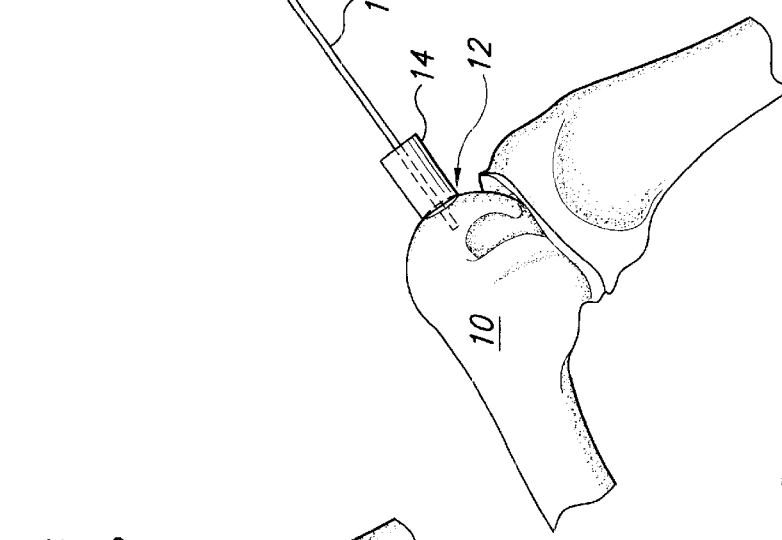
Figure 1:
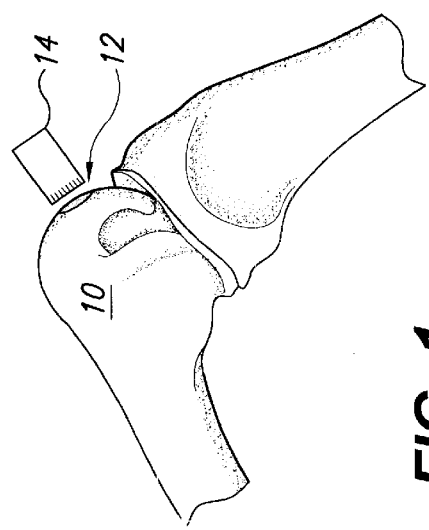
Figure 15:
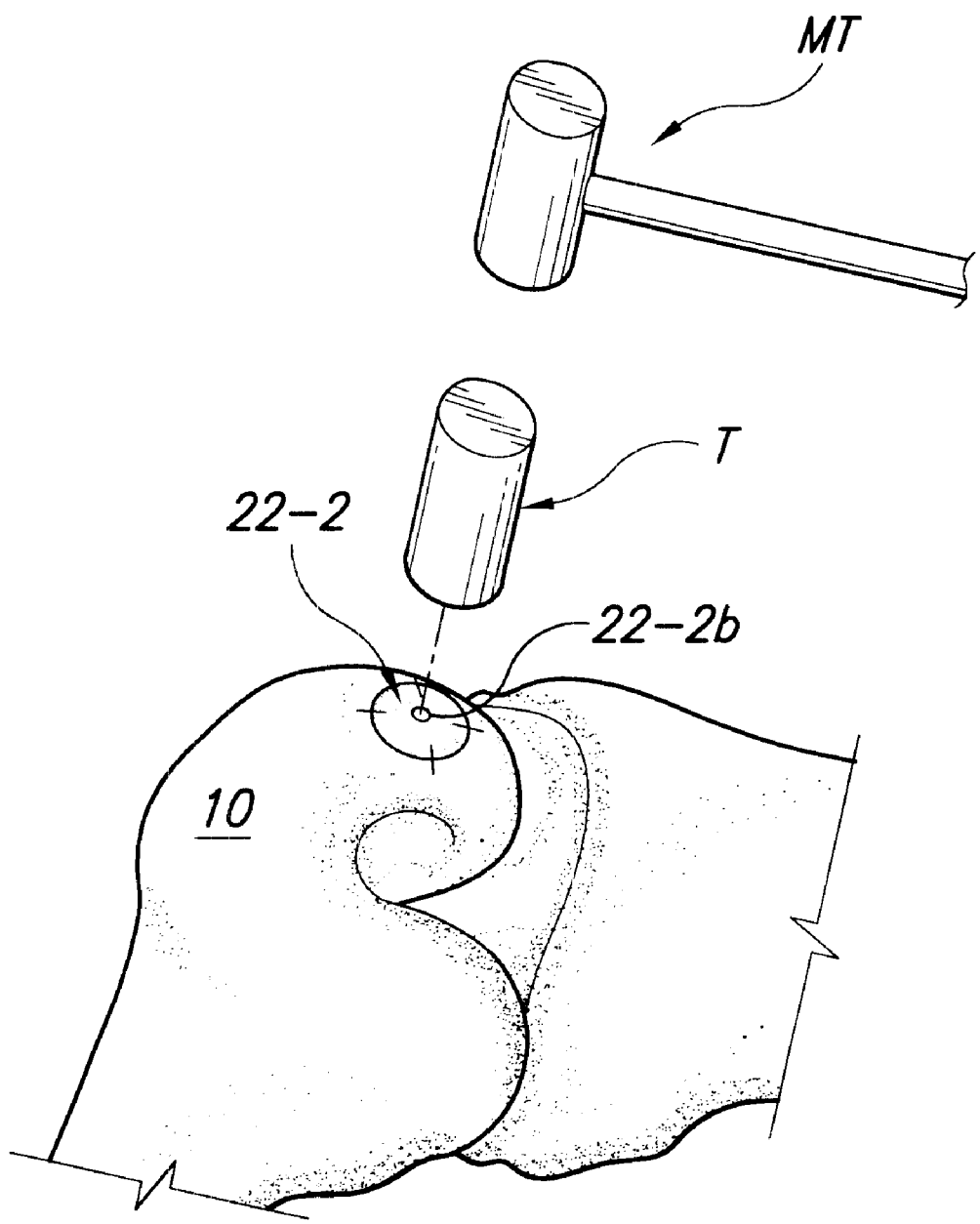

As shown in FIG. 2, the cutter/guide 14 is initially simply rested upon (not pushed against) the surface of the condyle 10. While in such an initial position (e.g., with the aid of a surgical assistant holding the cutter/guide 14 in place), the Steinmann pin 16 may then embedded into the condyle 10 to a depth of about 25 mm using a conventional surgical drill 18. Thus, the initial placement of the cutter/guide 14 is to orient the pin 16 perpendicular to the condylar surface. The cutter/guide 14 is thus removed from its contact with the condylar surface to leave the pin projecting outwardly therefrom as shown in FIG. 3.

A sterile workstation is set up with a vise 20. The allograft 22 is positioned within the vise 20 so as to be in the same orientation as the patient's exposed condyle 10. Specifically, as shown in FIGS. 4a and 4b, the orientation of the allograft 22 is such that an axis 24 perpendicular to the location of the donor section is parallel to the elongate pin 16 embedded in the patient's condyle 10. The cutter/guide 14 is then placed over the identical location on the allograft 22 as compared to the patient's condyle 10 as shown in FIG. 5a. A second Steinmann pin 26 is then inserted into the cutter/guide 14 as shown in FIG. 5b. The angle and location of the pin 26 is carefully compared to the angle and location of the pin 16 already embedded in the patient's condyle (i.e., compare the orientation of pins 16 and 26 in FIGS. 4b and 5b, respectively) and any orientation adjustments are made to ensure that the pins 16, 26 are substantially parallel to one another. The pin 26 may then be embedded in the allograft to a desired depth (e.g., about 26 mm) using the drill 18 (not shown in FIG. 5b, but see FIG. 2).

Prior to removing the cuffer/guide 14, its entire circumference is traced with an appropriate marker. The cutter/guide is then removed and hash marks are made through the marked circumference on the allograft 22 as shown in FIG. 6a to locate the North, South, East and West poles of the allograft plug 22-1. A similar marking technique is employed to mark the condyle plug 10-1 of the patient as shown in FIG. 6b. The North, South, East and West pole markings will be employed later to ensure proper orientation of the allograft plug 22-1. In this regard, the orientation of the markings on both the allograft 22 and the condyle 10 must be substantially identical to one another. If an orientation discrepancy exists, then the pin 26 may be reset in the allograft 22 and fresh markings for the plug 22-1 drawn. Once the orientations have been confirmed, the cutter/guide 14 is rotated by hand to drill through both the articulating surface of the patient's condyle 10 and the allograft 22 as shown in FIGS. 7a and 7b, respectively, until the cutter/guide 14 is against the cortical bone.

The same size drill bit and coring reamer 30 is then selected from the instrument kit. The drill bit 30 is mounted on the cannulated drill 18 and placed over the Steinmann pin 16 embedded in the patient condyle 10. The drill bit 30 is advanced through the articular surface of the condyle 10 while under constant irrigation from irrigator 32 and then through the cortical bone into the cancellous bone as depicted in FIG. 8a. It is preferably that the surgeon examine advancement of the drill bit 30 after every 2–3 mm of depth. Proper depth of cut is achieved when the minimum of cancellous bone along the perimeter is between about 3 to about 4 mm as shown in FIG. 8b, for example.

An apertured push-out plate (not shown) is first inserted over the pin 26 embedded in the allograft 22, and the allograft is then cored using the coring/reamer bit 34 attached to the cannulated drill 18. While under constant irrigation from the irrigator 32, the bit 34 is advanced into the allograft 22 approximately 25 mm (i.e., as determined by the depth marking 34-1 on bit 34) as shown in FIG. 8c. Care should be taken to not advance the bit 34 completely through the allograft 22. The bit 34 is slowly removed from the allograft 22 while under forward rotation and constant irrigation from the irrigator 32.

The once drilled with the bit 34, the allograft 22 is reoriented substantially vertically and the pin 26 removed therefrom. The plug 22-1 is excised by transecting the allograft 22 with an oscillating saw (not shown) approximately 20 mm below the allograft's surface. The initially drilled plug 22-1 should be steadied manually during transection to prevent it from abrupt dislocation.

The depth locations on the North, South, East and West poles (which may or may not be substantially equivalent to one another) corresponding to the respective depths of the prepared site cavity 10-2 (see FIG. 8b) on the patient's condyle are marked on the plug 22-1 as shown in the left-hand representation of FIG. 9. The depth markers at the poles may then be connected to form a circumferential mark M at the proper plug depth.

A set of locking pliers P are then used to grip securely the marked allograft plug 22-1 such that the circumferential depth marking M is located immediately above the surface of the jaws of the pliers P as shown in FIG. 10. Thereafter, using the jaw faces of the pliers P as a cutting guide, an oscillating saw blade S is advanced from the outside perimeter inwardly along the depth marking M as shown in FIG. 11.

The severed allograft plug (now identified in FIG. 12 by reference numeral 22-2 is removed from the pliers P. The bottom edge 22-2a is preferably chamfered to assist in fitting the plug 22-2 into the cavity site 10-2. In this regard, articular cartilage on the patient's condyle 10 may slightly migrate to interfere with the press fit dimensions of the plug 22-2 within the site cavity 10-2. Thus, the excess cartilage should be removed by reusing the cutter guide 14 along the interior perimetrical edge of the cavity site 10-2 as shown in FIG. 13.

The plug 22-2 is oriented so that its North, South, East and West pole markings match the North, South, East and West pole markings on the patient's condyle 10 as shown in FIG. 14. Any abnormality in shape and/or tissue material that may interfere with the fit of the plug 22-2 within the cavity site 10-2 should be corrected prior to final insertion. The plug 22-2 is press-fit into cavity 10-2 by advancing the former into the latter using a cannulated tamping tool T (see FIG. 15). A small mallet may be used in combination with the tamping tool T in order to forcibly push the plug 22-2 into the cavity site 10-2 on the patient's condyle 10. Care should be taken to ensure that all edges of the plug 22-2 advance substantially equally into the cavity site 10-2 and that the plug 22-2 does not become angularly canted. Any fragmentary cartilage is then removed around the perimeter of the plug 22-2 once seated within the cavity site 10-2. The allograft plug 22-2 may then be secured by using a low profile headless surgical screw positioned within the central hole 22-2b (see FIG. 12) which remains after removal of the pin 26.

The various instruments and implements employed in the osteochondral allograft transplant described above are most preferably supplied in kit form. Thus, in accordance with another aspect of this invention, the kit will necessarily include the elongate pins 16, 26 which may be inserted into the patient's condyle 10 and the allograft 22 as described previously. The kit may also contain a sterile clamp 20 so that the allograft 22 with the pin 26 embedded therein may be positionally fixed in parallel to the pin 16 embedded in the patient's condyle 10. Multiple coring/reamer bits 30 and/or 34 having different diameters and/or depths may be provided in the kit of this invention to allow the attending surgeon to form a wide range of cavity sites 10-2 and/or allograft plugs 22-2 to suit the particular patient's needs.

As noted previously, the use of the pin 26 in the embodiment described above with reference to FIGS. 1–15 will create a central hole 22-2b (see FIG. 12) which remains after removal of the pin 26 and may be used to provide a site for a low profile headless surgical screw. However, it may be desirable to harvest an allograft plug without such a central hole 22-2b. As shown in accompanying FIGS. 16–19, such an allograft plug may be obtained utilizing an annular guide collar 50 and elongate pins 52 in concert with the drill bit 34 described previously.

Figure 16:
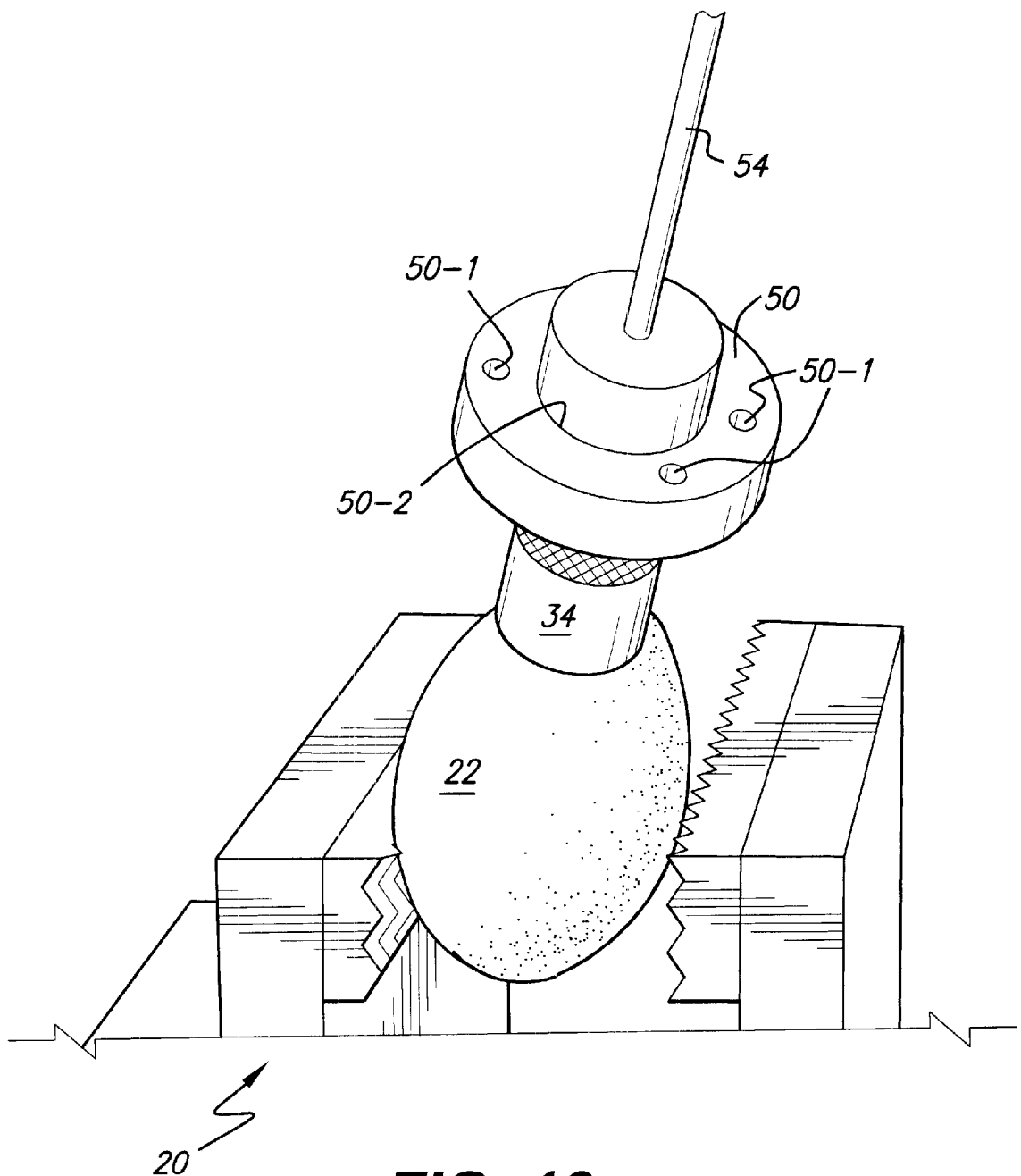
Figure 17:
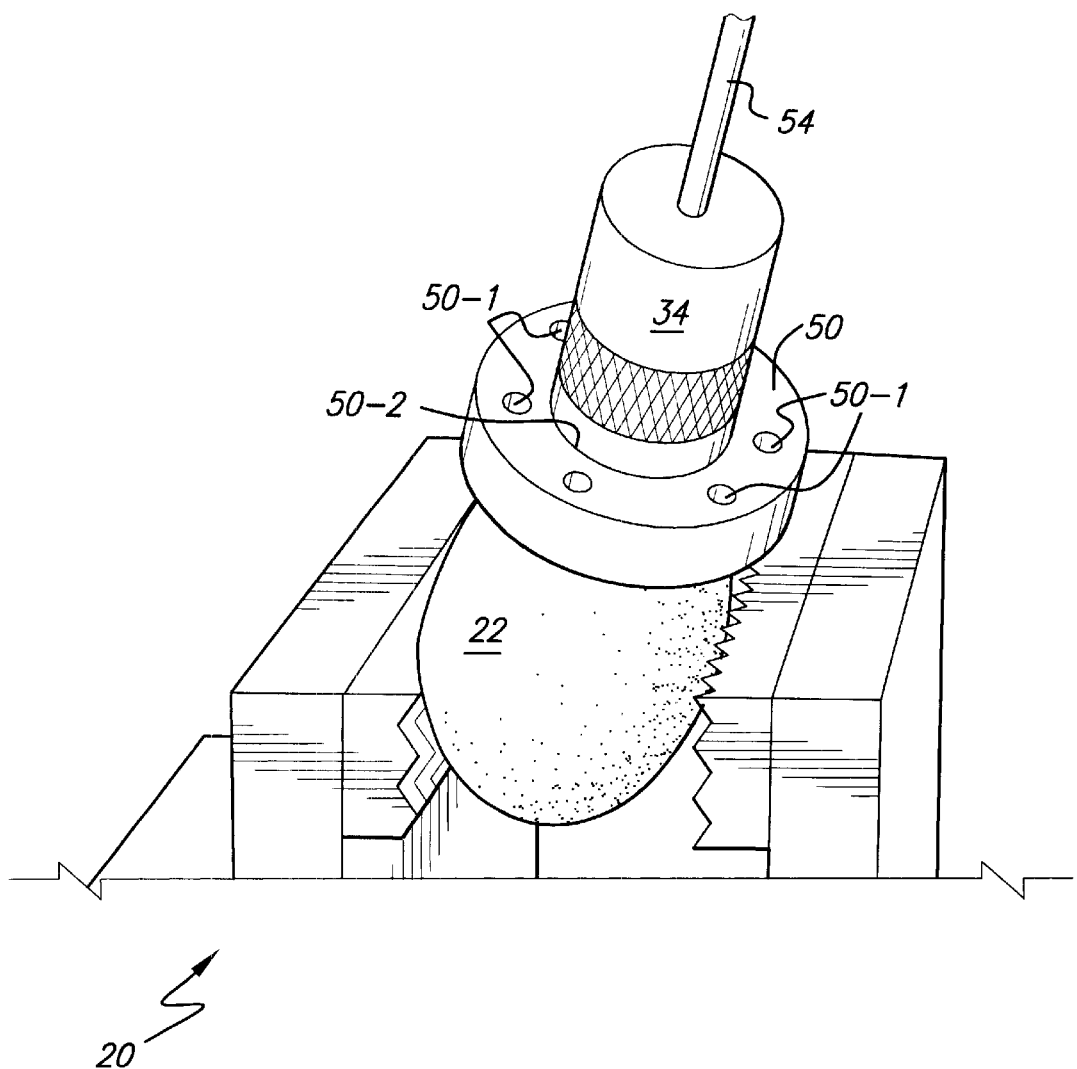

More specifically, as shown in FIG. 16, a drive pin 54 connected operatively to the drill 18 at its proximal end (see FIG. 19) and to the drill bit 34 at is distal end is positioned in substantial parallel alignment with the guide pin 16 (i.e., in a manner similar to that described previously). The drill bit 34 will thus be placed on the surface of the allograft 22 and will circumscribe an area thereon which will match closely the area on the patient's condyle to be replaced. With the drill bit 34 thereby positioned, an annular guide collar 50 is sleeved over the external surface of the drill bit until it is positioned against the surface of the allograft (see FIG. 17).

Figure 18:
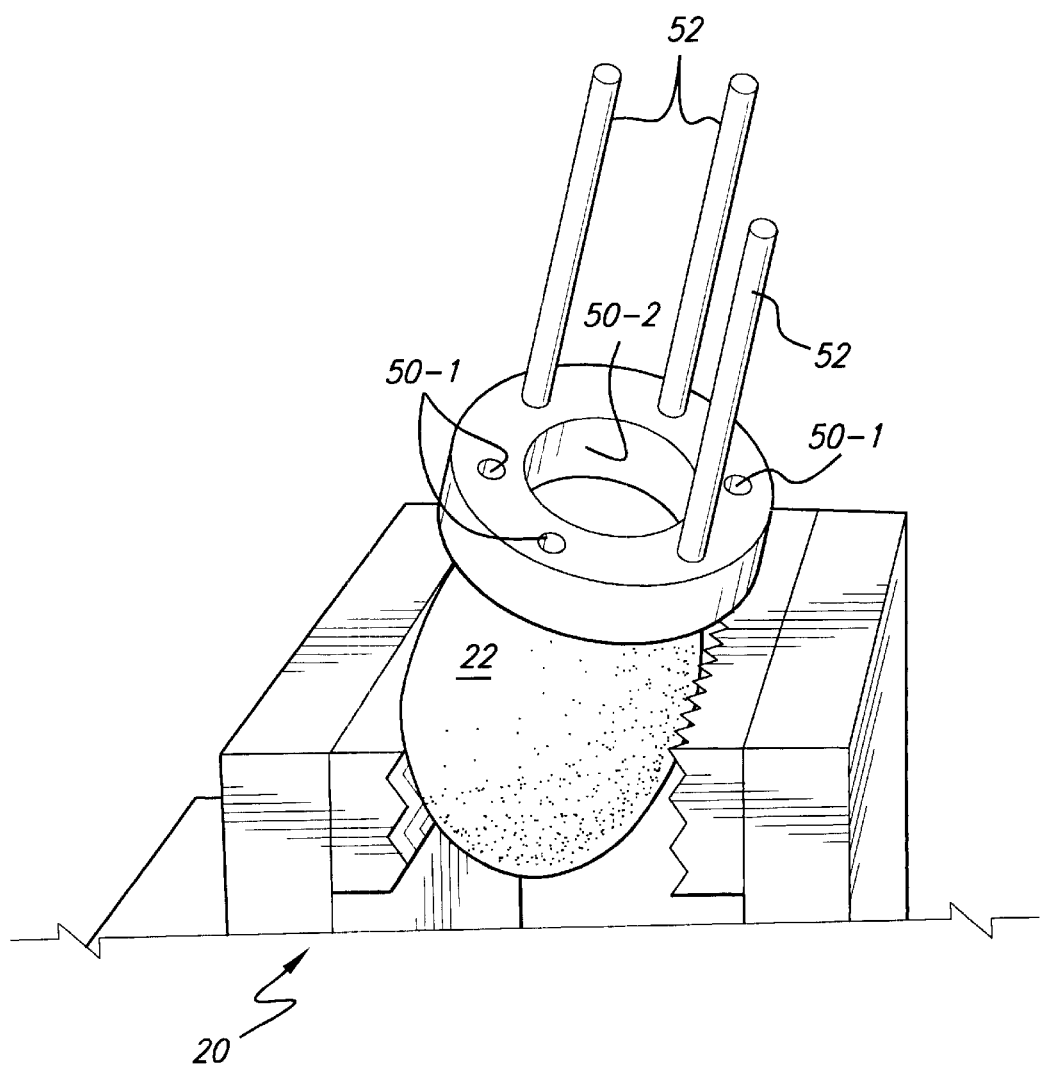
Figure 19:
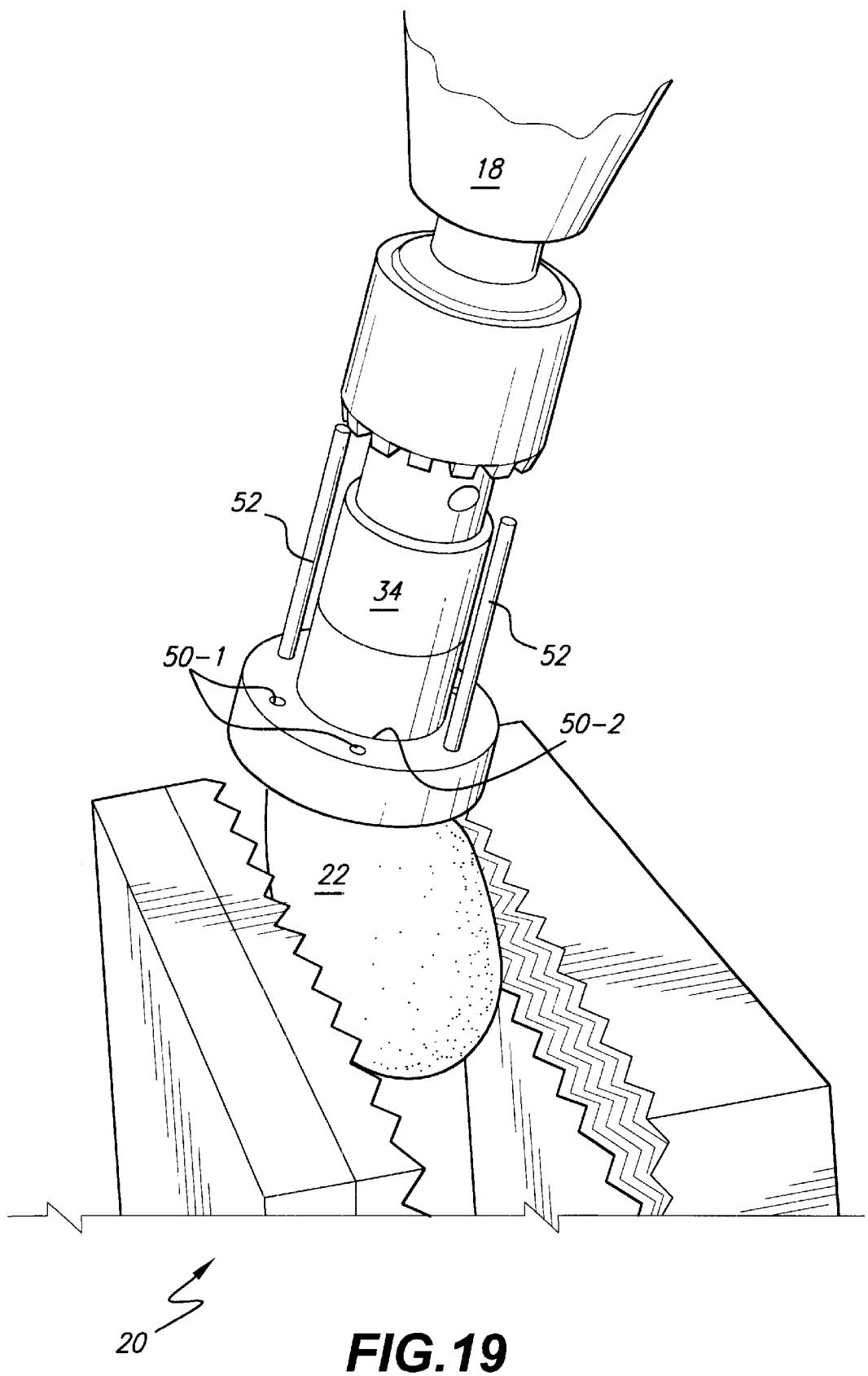

A series of elongate pins 52 may then be passed through respective guide apertures 50-1 of the collar 50 and secured into the allograft 22 thereby immobilizing the collar 50 (see FIG. 18). Thereafter, as shown in FIG. 19, the drill 18 may be operatively coupled to the drill bit 34. The drill bit 34 can then be positioned within the central aperture 50-2 of the collar 50 and operated so as to cut a plug of desire depth from the allograft 22. In such a manner, the central aperture 50-2 of the collar serves as a structural guide to the drill bit 32 since their respectively diameters are in close conformance to one another. The allograft plug may then be removed as described above and will not evidence any central hole 22-2b therein (i.e., since the pin 26 is not employed with this embodiment of the invention.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of transplanting an osteochondral allograft comprising the steps of:
   (a) placing an osteochondral allograft in substantially the same orientation as a patient condyle;
   (b) removing a transplantable plug from the allograft and forming a corresponding cavity site at a condylar defect in the patient condyle while maintaining said substantially same orientation therebetween; and thereafter
   (c) inserting the transplantable allograft plug into the cavity site in the patient condyle.

2. The method of claim 1, wherein step (a) includes:
   (a1) inserting a first elongate pin into the patient condyle at a condylar defect site;
   (a2) inserting a second elongate pin into the allograft; and
   (a3) positionally fixing the allograft such that said first and second pins are in substantial parallel alignment with one another.

3. The method of claim 2, wherein step (a3) includes positionally fixing the allograft in sterile clamp.

4. The method of claim 2 or 3, wherein step (a2) includes positioning an annular guide collar on a surface of the allograft, and thereafter positionally fixing said annular guide collar to said allograft surface by inserting at least one second elongate pin.

5. The method of claim 4, wherein step (b) includes:
   (b1) coring a section of the allograft to a predetermined depth by positioning a drill bit within a central aperture of said annular guide collar.

6. The method of claim 5, wherein step (b) includes:
   (b2) transecting the allograft substantially perpendicularly to the cored section to thereby release the cored section from the allograft and obtain said transplantable plug.

7. The method of claim 1, wherein step (b) includes:
   (b1) coring a section of the allograft to a predetermined depth.

8. The method of claim 7, wherein step (b) includes:
   (b2) transecting the allograft substantially perpendicularly to the cored section to thereby release the cored section from the allograft and obtain said transplantable plug.

9. The method of claim 2, which includes prior to step (b) the step of marking the condylar defect site and a region of the allograft from which the plug is to be removed with respective orientation marks.

10. The method of claim 2, which includes severing a section of the transplantable plug to conform to the predetermined depth of said cavity site.

11. The method of claim 10, which includes chamfering a bottom circumferential edge of the plug section.

12. The method of claim 11, wherein step (c) includes matching the orientation marks of the transplantable plug with the orientation marks of the cavity site, and then seating the plug within the cavity site in a press-fit relationship.

* * * * *